United States Patent
Makino et al.

(10) Patent No.: US 6,713,255 B1
(45) Date of Patent: Mar. 30, 2004

(54) DNA CHIP, PNA CHIP, AND THEIR PREPARATION METHODS

(75) Inventors: Yoshihiko Makino, Asaka (JP); Yoshihiko Abe, Asaka (JP); Makoto Takagi, Fukuoka (JP); Shigeori Takenaka, Koga (JP); Kenichi Yamashita, Fukuoka (JP); Masashi Ogawa, Tokyo (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 172 days.

(21) Appl. No.: 09/589,221

(22) Filed: Jun. 7, 2000

(30) Foreign Application Priority Data

Jun. 7, 1999 (JP) .......................................... 11-159338

(51) Int. Cl.[7] ................................................. C12Q 1/68
(52) U.S. Cl. ........................... 435/6; 435/7.1; 435/91.1; 435/91.2; 435/287.1; 536/22.1; 536/23.1; 536/24.3; 536/24.31; 536/24.32; 536/24.33
(58) Field of Search ............................ 435/6, 7.1, 91.1, 435/91.2, 287.1; 536/22.1, 23.1, 24.3–24.33

(56) References Cited

U.S. PATENT DOCUMENTS

| 5,942,397 | A | * | 8/1999 | Tarlov et al. | .................. | 435/6 |
| 6,127,129 | A | * | 10/2000 | Corn et al. | .................... | 435/6 |
| 6,261,782 | B1 | * | 7/2001 | Lizardi et al. | ................. | 435/6 |
| 6,410,229 | B1 | * | 6/2002 | Lockhart et al. | ............... | 435/6 |

OTHER PUBLICATIONS

Takenaka Chem Commun. pp. 1111–1112 1998.*

* cited by examiner

*Primary Examiner*—Jeffrey Siew
(74) *Attorney, Agent, or Firm*—Reed Smith LLP

(57) ABSTRACT

A DNA chip (or PNA chip) composed of a solid carrier and plural DNA fragments (or PNA fragments) fixed onto is the solid carrier at each one end, wherein a plurality of short chain spacer molecules having a hydrophilic moiety at each one end are fixed at each another end onto a surface of the solid carrier having no DNA fragments (or no PNA fragments) on its surface is effective for high sensitive quantitative analysis of a nucleic acid fragment complementary to the DNA fragment (or PNA fragment).

5 Claims, 2 Drawing Sheets

DNA CHIP, PNA CHIP, AND THEIR PREPARATION METHODS

FIELD OF THE INVENTION

This invention relates to a DNA chip or a PNA chip favorably employable for detecting, with high sensitivity, a nucleic acid fragment complementary to a DNA fragment or a PNA fragment of the DNA chip or the PNA chip, respectively. The invention further relates to a method of quantitative analysis of a nucleic acid fragment contained in a liquid sample in an extremely small amount using a DNA chip or a PNA chip which has a DNA fragment or a PNA fragment, respectively, on its solid carrier.

BACKGROUND OF THE INVENTION

Detection of a nucleic acid fragment is generally made using a probe DNA which is complementary to the nucleic acid fragment to be detected, by way of hybridization. The probe DNA is generally fixed onto a solid carrier (substrate) to give a DNA chip. In more detail, a nucleic acid fragment in a sample liquid is once labelled with a fluorescent label or a radioisotope label, and then the sample liquid is brought into contact with the probe DNA of the DNA chip If the labelled nucleic acid fragment in the sample liquid is complementary to the probe DNA, the labelled nucleic acid fragment is combined with the probe DNA by hybridization. The labelled nucleic acid fragment fixed onto the DNA chip by hybridization with the probe DNA is then detected by an appropriate detection method such as fluorometry or autoradiography. The DNA chip is widely employed in gene technology, for instance, for detecting a complementary nucleic acid fragment or sequencing a nucleic acid.

The DNA chip is described, for instance, in Fodor S. P. A., Science, 251, 767(1991) and Schena M., Science, 270, 467(1995). The DNA chip is understood to efficiently detect a small amount of a complementary nucleic acid fragment in a small amount of a sample liquid. However, the heretofore known DNA chip has a limitation on the detection level of nucleic acid fragment such as a level of not less than $10^{-19}$ mol./dot. in certain cases, an improved high sensitive detection is required. For instance, a procedure for monitoring of gene expression, particularly gene expression of a low level, a procedure for analyzing a gene variation, and a procedure for analyzing gene polymorphism, require higher sensitivity in the detection of complementary nucleic acid fragments.

Detection of nucleic acid fragment using an electrochemical label is also known (Japanese Patent Provisional Publication No. 9-288080, and a preprint of the 57th Analytical Chemistry Conference pp. 137–138 (1996)). The electrochemical label such as N-hydroxysuccinimide ester of ferrocenecarboxylic acid is attached to a probe DNA. The probe DNA is fixed onto an electroconductive substrate having an output terminal. In the detection procedure, a sample liquid containing the target nucleic acid fragment is brought into contact with the probe DNA having the ferrocene derivative label in the presence of an electrochemically active thread intercalator. The target nucleic acid fragment, if it is complementary to the probe DNA, is hybridized with the probe DNA. Into the formed hybrid structure, the electrochemically active thread intercalator is intercalated. Thereafter, a potential is applied to the electroconductive substrate to measure an electric current flowing through the ferrocene derivative label and the thread intercalator.

On the above-mentioned electroconductive substrate are fixed the ferrocene derivative-modified DNA fragments of approximately $10^{-11}$ mol., per 1 mm$^2$ of surface area of the substrate). It is described that complementary nucleic acid molecules in the range of $10^{-15}$ to $10^{-11}$/mm$^2$ are detected, when a sample liquid containing target nucleic acid molecules is brought into contact with the probe DNA.

Preprint of the 47th Polymer Society Conference, pp. 3155–3156 (1998) describes an electrochemical detection method in which a sample liquid containing a target nucleic acid fragment is brought into contact a DNA probe fixed onto an electroconductive substrate in the presence of an electrochemically active thread intercalator. On the electroconductive substrate are fixed the DNA probes in an amount of approximately $10^{-11}$ mol./2 mm$^2$ (surface area of substrate). If a sample liquid containing target nucleic acid fragments in an excessive amount (such as approximately ten times or more) is brought into contact with the probe DNA, complementary nucleic acid fragments in an amount of approximately $10^{-11}$ mol. are detected.

P. E. Nielsen et al., Science, 254, 1497–1500(1991) and P. E. Nielsen et al., Biochemistry, 36, pp.5072–5077 (1997) describe PNA (Peptide Nucleic Acid or Polyamide Nucleic Acid) which has no negative charge and functions in the same manner as DNA does. PNA has a polyamide skeleton of N-(2-aminoethyl)glycine units and has neither glucose units nor phosphate groups. A representative PNA as well as a representative DNA are illustrated below:

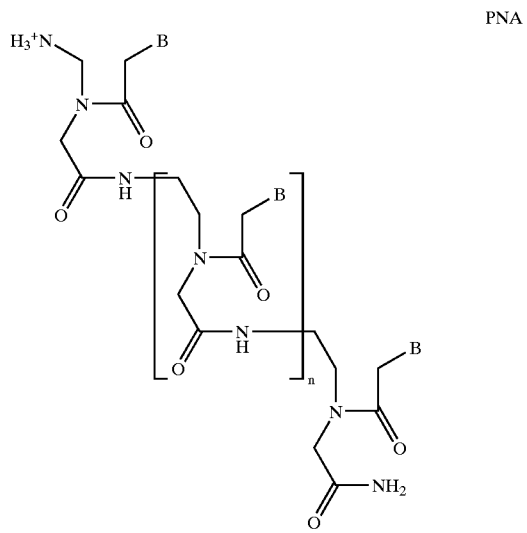

PNA

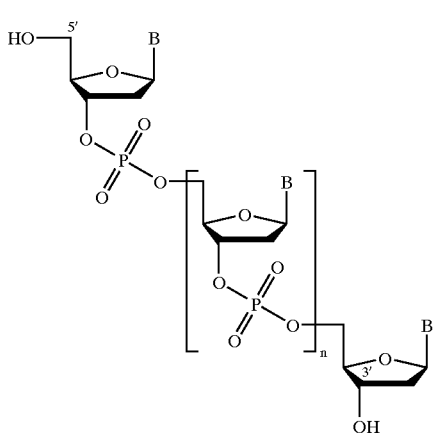

Since PNA is electrically neutral and is not charged in the absence of an electrolytic salt, PNA is able to hybridize with a complementary nucleic acid fragment to form a hybrid which is more stable than hybrid given by a DNA prove and its complementary nucleic acid fragment (Preprint of the 74th Spring Conference of Japan Chemical Society, pp. 1287, reported by Naomi Sugimoto).

Japanese Patent Provisional Publication No. 11-332595 describes a PNA probe fixed on a solid carrier at its one end and a detection method utilizing the PNA probe The PNA probe is fixed onto the solid carrier by the avidin-biotin method.

The aforementioned P. E. Nielsen et al., Science, 254, 1497–1500(1991) also describes a PNA probe labelled with isotope element and a detection method of a complementary nucleic acid fragment.

Since the PNA probe shows no electric repulsion to a target nucleic acid fragment in a sample liquid, an improved high detection sensitivity is expected.

SUMMARY OF THE INVENTION

It is an object of the present invention to provide a nucleic acid fragment-detecting means showing an improved high sensitivity for a nucleic acid fragment contained in a sample liquid.

Specifically, it is an object of the invention to provide a DNA chip and a PNA chip which are employable for quantitatively detecting a nucleic acid fragment contained in a sample liquid in an extremely small amount.

It is another object of the invention to provide a method for quantitatively detecting, with a high sensitivity and good reproducibility, a nucleic acid fragment contained in a sample liquid in an extremely small amount.

The present invention resides in a DNA chip comprising a solid carrier and a plurality of DNA fragments fixed onto the solid carrier at each one end, wherein a plurality of short chain spacer molecules having a hydrophilic moiety at each one end are fixed at each another end onto a surface area of the solid carrier having no DNA fragments thereon.

The invention further resides in a PNA chip comprising a solid carrier and a plurality of PNA fragments fixed onto the solid carrier at each one end, wherein a plurality of short chain spacer molecules having a hydrophilic moiety at each one end are fixed at each another end onto a surface area of the solid carrier having no PNA fragments thereon.

The DNA chip (or PNA chip) of the invention is favorably prepared by a process comprising the steps of:
  applying onto a solid carrier an aqueous solution of a plurality of DNA fragments (or PNA fragments) dissolved or dispersed in an aqueous medium to fix the DNA fragments (or PNA fragments) onto the solid carrier; and
  applying onto the solid carrier having thereon the fixed DNA fragments (or PNA fragments) an aqueous solution of short chain spacer molecules having at each one end a hydrophilic moiety and at each another end a moiety reactive to fix to the solid carrier.

In the DNA chip and PNA chip of the invention, the solid carrier preferably is an electro-conductive substrate.

The DNA chip (or PNA chip) of the invention is favorably employed in a method of quantitative analysis of a nucleic acid fragment contained in a sample liquid which is complementary to the DNA fragments (or PNA fragments) of the DNA chip (or PNA chip), which comprises the steps of:
  adjusting the concentration of the nucleic acid fragment in the sample liquid so that a droplet of the sample liquid applied to the DNA chip (or PNA chip) should contain $10^{-20}$ to $10^{-16}$ mol. of the nucleic acid fragment per 1 $mm^2$ of the surface of the electro-conductive substrate of the DNA chip (or PNA chip);
  bringing the nucleic acid concentration-adjusted sample liquid into contact with the DNA chip (or PNA chip) having an electroconductive substrate, whereby hybridizing the nucleic acid with the DNA fragment (or PNA fragment) on the DNA chip (or PNA chip);
  bringing an electrochemically active molecule in contact with the hybridized nucleic acid and DNA fragment (or PNA fragment), whereby attaching the electrochemically active molecule to the hybridized nucleic acid and DNA fragment (or PNA fragment);
  applying a potential to the DNA chip (or PNA chip); and
  measuring an electric current flowing from or to the electro-conductive substrate through the attached electrochemically active molecule.

Accordingly, the DNA chip (or PNA chip) of the invention is preferably supplied in the form of a kit for conducting quantitative analysis of a nucleic acid fragment contained in a sample liquid which is complementary to the DNA fragments (or PNA fragments) of the DNA chip (or PNA fragment), which comprises the DNA chip (or PNA chip) having an electroconductive substrate and an electrochemically active molecule which is attachable to a hybridized nucleic acid fragment and DNA fragment.

In the DNA chip (or PNA chip) of the invention, the DNA fragments (or PNA fragments) are preferably fixed on the solid carrier in an amount of $10^{-20}$ to $10^{-12}$ mol./$mm^2$.

The hydrophilic moiety of the spacer molecule preferably is a hydroxyl group, and the spacer molecule is preferably fixed on the solid carrier through a mercapto moiety attached to the end of the spacer molecule. The spacer molecule is preferably derived from a compound selected from the group consisting of 2-mercaptoethanol, 3-mercaptoethanol, 6-mercaptoethanol, and N,N'-di(3-hydroxy-n-propyl)imidazole-2-thione. The spacer molecule may contain a cyclic group in the molecular structure.

DETAILED DESCRIPTION OF THE INVENTION

Figure 1:
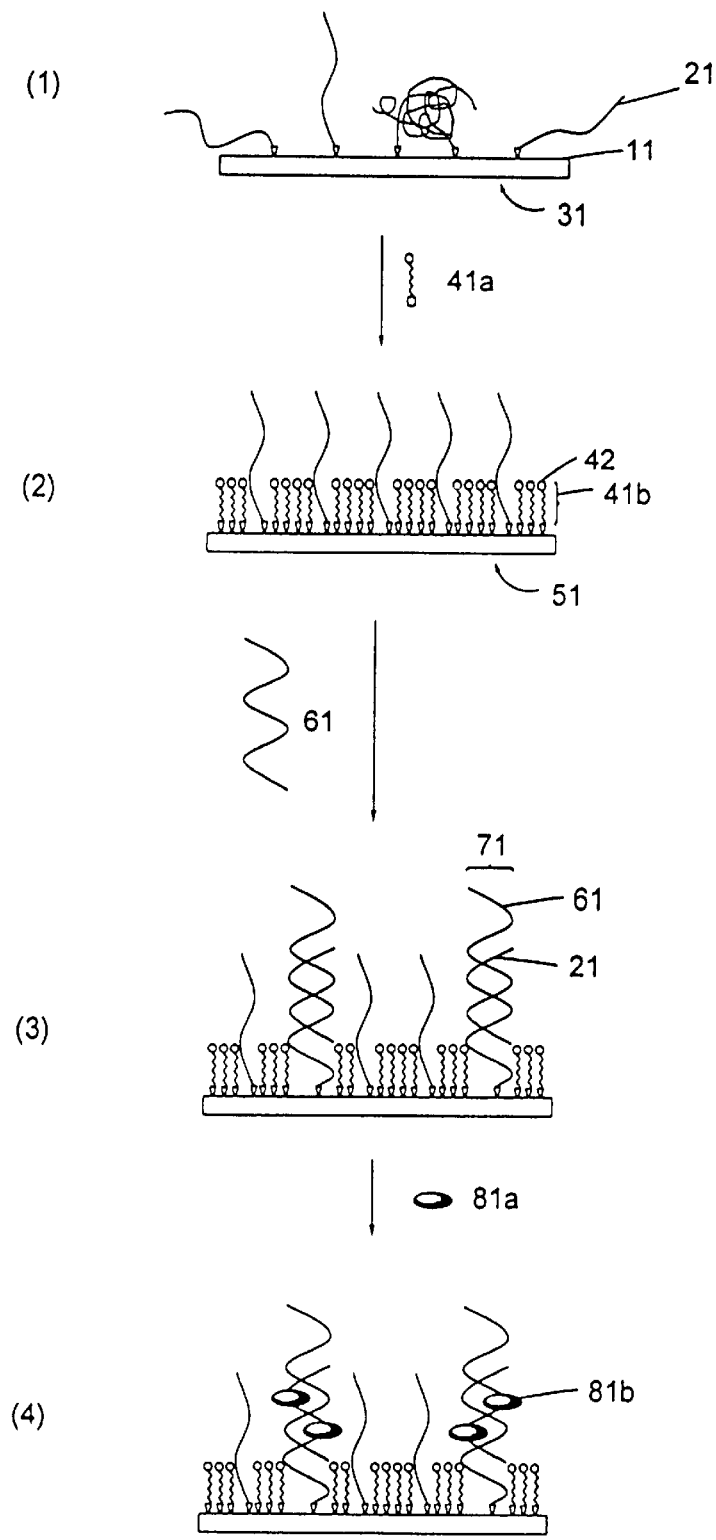
FIG. 1 schematically shows a DNA chip (or a PNA chip) of the invention and a mechanism of the detection of complementary nucleic acid fragments according to the invention.

The DNA chip and PNA chip according to the invention are described, in more detail, by referring to FIG. 1. Since the DNA chip and PNA chip have essentially the same structure, the following description is mainly addressed to the structure and preparation of the DNA chip.

FIG. 1-(1) schematically illustrates a conventionally employed DNA chip 31 which comprises a solid carrier (eg., electroconductive substrate) 11 and a plurality of DNA fragments 21 fixed onto the solid carrier at each one end.

FIG. 1-(2) schematically illustrates a DNA chip 51 of the invention which is prepared by bringing an aqueous solution containing a plurality of spacer compounds (or mask compounds, which has a short chain structure, as compared with the chain structure of the previously fixed DNA fragment) 41a into contact with the DNA chip 31 of FIG. 1-(1) so that the plural spacer compounds 41a are attached to the solid carrier 11 in the areas where the DNA fragments are not fixed. The fixed spacer compounds (namely, spacer molecules) 41b have a hydrophilic group 42 on each of their free terminal ends.

Solid Carrier

The solid carrier of the DNA chip of the invention can be any of known solid carriers or their equivalent materials, for instance, an electroconductive substrate (e.g., electrode), a plastic sheet, and a glass sheet The electroconductive substrate is generally employed for conducting the electrochemical analysis.

The electroconductive substrate may be provided on an electro-insulative support material. The electroconductive substrate and the support material preferably have a less hydrophilic surface or a hydrophobic surface. The electroconductive substrate may have a plain surface or a surface having many fine concaves and convexes.

The electro-insulative support material can be prepared from glass, ceramics, polymer materials (e.g., polyethylene terephthalate, cellulose acetate, polycarbonate of Bisphenol A, polystyrene, poly(methyl methacrylate), silicon, active carbon, and porous materials (e.g., porous glass, porous ceramics, porous silicon, porous active carbon, cloth, knitted cloth, non-woven cloth, filter paper, and membrane filter). Polymer materials, glass, and silicon are preferably employed.

Generally, the electro-insulative support material is employed in the form of a sheet (or a film). The sheet of the support material preferably has a thickness in the range of 100 to 1,000 $\mu$m.

The electroconductive substrate can be made of electrode material, optical fiber, photodiode, thermistor, piezo electrical element, or surface elasticity element. The electrode material is generally employed. The electrode can be carbon electrode of graphite or glassy carbon, noble metal electrode of platinum, gold, palladium, or rhodium, metal oxide electrode of titanium dioxide, tin oxide, manganese oxide, or lead oxide, semiconductor electrode of Si, Ge, ZnO, or Cds, or electron conductor of titanium. Preferred are glassy carbon electrode and gold electrode The electrode may be covered with electroconductive polymer film or monomolecular film.

The DNA chip of the invention is preferably composed of a hydrophobic, electro-insulative support material, a plurality of hydrophobic electroconductive substrates placed on the support material, a plurality of DNA fragments fixed on each of the electroconductive substrates, and a plurality of spacer molecules fixed on the substrates at free areas (i.e., areas where no DNA fragments are present). Each of the electroconductive substrates is preferably arranged apart from the adjoining electroconductive substrates so that each substrate is insulated from the adjoining substrates. The electroconductive substrate may be placed on the support material via an intermediate layer such as a hydrophilic intermediate layer which may have electron charges.

An example of the structure composed of an electro-insulative support material and a plurality of electrodes arranged on the support material is a silicon chip described in Sosnowski, R. G., et al., Proc. Natl. Acad. USA, 94, 1119–1123(1997). The electrode may be produced on a polymer film using a composite sheet of a polymer film and a metal film.

DNA Fragment

DNA fragment to be fixed onto the solid carrier may be polynucleotide such as cDNA, a portion of cDNA, or EST. The polynucleotide is favorably employed for studying gene expression. Otherwise, DNA fragment to be fixed onto the solid carrier may be oligonucleotide, which is favorably employed for studying variations and polymorphism of gene. The DNA fragment to be fixed onto the solid carrier preferably is one of 3 to 50 mers, more preferably 10 to 25 mers.

If the DNA chip of the invention comprises plural DNA chip units each of which has an electroconductive substrate (e.g., electrode) and DNA fragments fixed onto the substrate, the plural DNA chip units can have the same DNA fragments or different DNA fragments.

Fixation of DNA fragments onto the substrate can be done by any of known methods. For instance, DNA fragments having a reactive group on one end can be fixed onto the substrate through covalent bond by the reaction of the reactive group and the functional group of the surface of the substrate. For instance, a mercapto group is attached to DNA fragment at its 5'- or 3'-terminal, and the mercapto group is then caused to react with a gold electrode, so that an electroconductive substrate having DNA fragments fixed thereon is produced. The procedure for attaching a mercapto group to DNA fragments is described in M. Maeda, et al., Chem. Lett., 1805–1808(1994) and B. A. Connolly, Nucleic Acids Res., 13, 4484(1985).

If the electroconductive substrate is made of glassy carbon electrode, the glassy carbon electrode is oxidized by potassium permanganate to produce a carboxylic acid group on the electrode. The carboxylic acid group on the electrode forms an amide bonding with DNA fragment so that the DNA fragment is fixed onto the substrate. See K. M. Millan, et al., Analytical Chemistry, 65, 2317–2323(1993).

DNA fragments can be fixed to the substrate, initially, in the form of hybrid DNA fragments For instance, the hybrid DNA fragments are combined with a mercapto group at their 5'- or 3'-terminals (preferably 5'-terminals) of their single fragment, and are brought into contact with a gold electrode, so that the hybrid DNA fragments are fixed on the electrode. The hybrid DNA fragment fixed on the electrode is then processed to dissociate a single fragment having no mercapto group, so that the desired DNA chip is produced.

The covalent bond between the DNA fragment and the substrate can be formed using an amino group, an aldehyde group, a mercapto group, or a biotin molecule which is attached to the DNA fragment. If the substrate is made of glass sheet or silicon sheet, its surface is preferably treated with a silane coupling agent, prior to the formation of covalent bond.

Otherwise, DNA fragments can be synthesized on the substrate by a known method.

The DNA fragment having a reactive group on one end can be fixed onto a solid carrier such as an electroconductive substrate by spotting onto the carrier an aqueous solution containing the DNA fragment. The aqueous solution preferably contains the DNA fragment in a concentration of several pM to several mM. The volume for the spotting generally is in the range of 1 to 100 nL, preferably 1 to 10 nL. The aqueous solution may contain a viscosity increasing additive such as sucrose, polyethylene glycol, or glycerol. The spotting can be made manually or utilizing a commercially available spotter. The spotted solution is then kept on the solid carrier at a predetermined temperature for several hours (namely, incubation), whereby the DNA fragment is fixed onto the carrier by covalent bonding. After the incubation is complete, free DNA fragment (which is not fixed onto the carrier) is preferably washed out.

The DNA fragment is preferably fixed onto the solid carrier in an amount of $10^{-20}$ to $10^{-12}$ mol./mm$^2$ of the surface area of the carrier. The amount of the fixed DNA fragment can be determined by means of HPLC (high performance liquid chromatography) or other analytical apparatuses.

PNA Fragment

The PNA fragment preferably employable in the invention has the following formula (I):

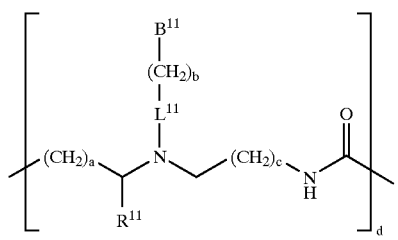

In the formula, the symbols of $B^{11}$, $R^{11}$, $L^{11}$, a, b, c, and d have the meanings described below.

$B^{11}$ is a ligand and represents one of bases of natural nucleic acids (i.e., A, T, C, G, I, or U) or its analogue. $B^{11}$ is bonded through the 9th position in the case that the base is a purine base such as adenine, guanine or inosine, and through the 1st position in the case that the base is a pyrimidine base such as thymine, uracil or cytosine. The base analogue is an organic base which is similar to the base of natural origin in its chemical structure, for instance, a base group which is prepared by replacing the carbon or nitrogen atom of the purine or pyrimidine ring with a nitrogen or carbon atom, respectively, or a base group modifying the purine or pyrimidine ring with a substituent such as a sulfhydryl group or a halogen atom. Otherwise, $B^{11}$ can be an aromatic moiety containing no nucleic acid base, an alkanoyl group having 1 to 4 carbon atoms, a hydroxyl group, or a hydrogen atom. Examples of the base analogues include 7-deazaadenine, 6-azauracil, and 5-azacytosine. $B^{11}$ also can be a DNA intercalator, a reporter ligand, a protein label such as hapten or biotin, a spin label, or a radioactive label. Particularly preferred are nucleic acid bases (i.e., A, T, C, G, and U).

$R^{11}$ is a hydrogen atom or a group derived from a side-chain of an α-amino acid of natural origin. Examples of such groups include an alkyl group having 1 to 6 carbon atoms, an aryl group having 6 to 20 carbon atoms, an aralkyl group having an alkyl group of 1 to 6 carbon atoms, a heteroaryl group having 6 to 20 carbon atoms, a hydroxyl group, an alkoxy group having 1 to 6 carbon atoms, an alkylthio group having 1 to 6 carbon atoms, a group of —NR$^{13}$R$^{14}$ [each of R$^{13}$ and R$^{14}$ independently is a hydrogen atom, an alkyl group having 1 to 3 carbon atoms, an alkoxy group having 1 to 3 carbon atoms, an alkylthio group having 1 to 3 carbon atoms, or a hydroxyl group], and a mercapto group. R$^{11}$ may form an alicyclic ring or a heterocyclic ring in combination with the carbon atom to which R$^{11}$ is attached.

$L^{11}$ is a linking group such as a divalent group represented by the group of —CO— or —CONR$^{12}$— [R$^{12}$ is a hydrogen atom, an alkylene group having 1 to 4 carbon atoms, a hydroxyl group, an alkoxy group having 1 to 4 carbon atoms, or an amino group], or an alkylene group having 1 to 4 carbon atoms. The alkoxy group and amino group may have one or more substituents such as alkyl of 1–4 carbon atoms, alkoxy of 1–4 carbon atoms, and hydroxyl.

Each of a, b and c independently is an integer of 0 to 5, preferably 1, and d is an integer of 1 to 60, preferably an integer of 1 to 40.

A particularly preferred PNA fragment has the following formula (II), in which each of $B^{11}$ and d has the same meaning as described above for the formula (I):

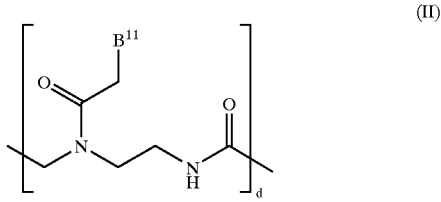

(II)

The PNA fragment can be fixed onto a solid carrier in a known manner (see Protein, Nucleic Acid, Enzyme, Vol. 43, No. 13, 2004–2011(1988) and Japanese Patent Provisional Publication 9-288080. Also employable are procedures similar to the aforementioned DNA fragment-fixing procedures.

Short Chain Spacer Molecules

The DNA chip of the invention has a plurality of short chain spacer molecules having a hydrophilic moiety at each one end which are fixed at each another end onto a surface area of the solid carrier having no DNA fragments thereon, as schematically illustrated in the attached FIG. 1-(2). The coverage of the solid carrier using the spacer molecules can be expressed in terms of "masking treatment".

The short chain of the spacer molecule means that the molecular length of the spacer molecule is sufficiently short, as compared with the length of the DNA fragment fixed onto the carrier in their vicinity.

The spacer molecule preferably has a main skeleton composed of an alkylene group having 1 to 6 carbon atoms. The spacer molecule may have a cyclic group in the molecular chain or as a substituent. Examples of the cyclic groups include an aryl group having 6 to 12 carbon atoms, a cycloalkyl group having 3 to 6 carbon atoms, and a heterocyclic group containing 1 to 4 hetero atoms (e.g., N, S, O, or P) and 2 to 20 carbon atoms. The cyclic group can contain the reactive group which can be reacted with the carrier surface to fix the spacer atoms to the carrier. One example is a imidazole-2-thione group.

The hydrophilic moiety can be attached to the spacer molecule in the terminal position or in the vicinity of the terminal position. One or more hydrophilic moieties may be attached to the spacer molecule. Examples of the hydrophilic moieties include hydroxyl, carboxyl, amido, phosphoryl, and sulfonyl. Preferred is hydroxyl.

The other end of the spacer molecule is fixed onto a surface area of the carrier where the DNA fragment is not attached. The fixation of the spacer molecule is preferably performed utilizing a reactive group which is attached to the spacer molecule at the other end. Examples of the reactive groups include mercapto, sulfide, disulfide, thiocarbonyl, and thiocarboxyl. Preferred are mercapto, thiocarbonyl, and sulfide. Most preferred is mercapto. It is also preferred that the solid carrier has a reactive group, on its surface, such as amino, imino, hydrazino, hydrazide, amide, carboxyl, aldehyde, epoxy, or peroxy.

Examples of the reactive compounds serving as the spacer molecules include mercaptomethanol, 2-mercaptoethanol, 3-mercaptopropanol, 4-mercaptobutanol, 5-mercaptopentanol, 6-mercaptohexanol, N,N'-di(3-hydroxy-n-propyl)imidazole-2-thione, and various imidazole-2-thione derivatives described in A. J. Arduengo, et al., J. Am. Chem. Soc., 1990, 112, 6153–6154. Preferred are 2-mercaptoethanol, 3-mercaptopropanol, 4-mercaptobutanol, 5-mercaptopentanol, and 6-mercaptohexanol. Most preferred is 2-mercaptoethanol. These active compounds may be in the form of their salts with sodium or potassium The alkylene chain of the active compound can be substituted with one or more substituents such as a hydrocarbyl group having 1 to 6 carbon atoms (e.g., methyl, ethyl, or phenyl).

Onto the solid carrier, two or more different spacer molecules can be provided.

Hybridization

The hybridization can be performed essentially in the same manner as that employed in various assay procedures utilizing the conventional DNA chip.

When the electrochemical analysis is performed, an electrochemically active molecule, specifically, an electrochemically active thread intercalator, is preferably employed for insertion into a hybrid formed by the DNA fragment and a sample nucleic acid fragment on the electroconductive substrate. The thread intercalator assists easy flowing of electric current from or to the substrate along the formed hybrid structure. The electrochemical thread intercalator can be present when hybridization takes place. Otherwise, the thread intercalator can be brought into contact with a previously formed hybrid structure. In the latter case, a free nucleic acid fragment which is not hybridized with the fixed DNA fragment is preferably removed from the substrate by washing with a mixture of a surfactant (preferably sodium dodecylsulfate) and a buffer (preferably a citrate buffer) in advance of the contact with the intercalator. The intercalator is preferably brought into contact with the hybrid in an aqueous solution at a concentration of 10 nM to 10 mM.

The hybridization is preferably performed at a temperature between room temperature and approximately 70° C., for 0.5 to 20 hours.

Sample Nucleic Acid Fragments

The sample nucleic acid fragment can be a DNA fragment obtained from a living sample, if necessary, after performing an appropriate procedure, a DNA fragment obtained by cleaving a DNA fragment produced by gene technology and isolating the cleaved product by electrophoresis, a single stranded-DNA fragment which is synthesized by a chemical process. A double stranded DNA fragment is preferably treated with heat or an alkaline solution to give a single stranded fragment. Plural kinds of nucleic acid fragments can be analyzed on one DNA chip.

The sample nucleic acid fragment is brought into contact with DNA fragment fixed on the solid carrier in the form of its aqueous solution. The aqueous solution preferably contains the sample nucleic acid fragment at a concentration of several pM to several mM, preferably at a concentration of several pM to several nM.

Electrochemically Active Thread Intercalator

The electrochemically active thread intercalators favorably employed for the electrochemical analysis of nucleic acid fragments are already known. A representative example of the intercalator is a thread intercalator having an electroconductive group at one end or both ends. The thread intercalator having the electroconductive group preferably has an oxidative-reductive activity. The oxidative-reductive activity can be imparted to the thread intercalator by incorporating into the intercalator a ferrocene group, a catechol amine group, a metal bipyridine complex group, a metal phenathroline complex group, or a viologen group. The intercalator moiety preferably comprises a naphthaleneimide moiety, an anthracene moiety, or an anthraquinone moiety. Preferred electrochemically active thread intercalator is a ferrocene-containing naphthalene diimide compound [NDIFc$_2$-1, which is prepared from carboxylic acid ester of N-hydroxysuccinimide and a corresponding amine compound, see S. Takenaka et al., J. Chem. Soc. Commun., 1111 (1998)]:

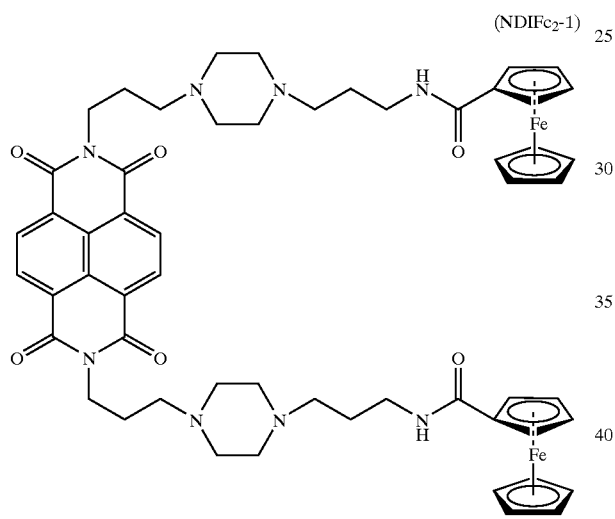

(NDIFc$_2$-1)

A ferrocene-containing naphthalene diimide derivative having the following formula is also preferably employed:

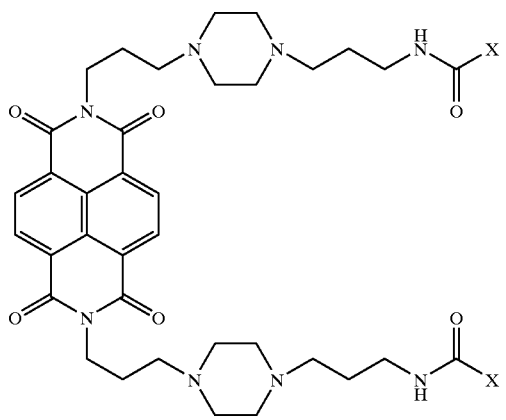

In the above-illustrated formula: X is one of the following ferrocene derivative groups:

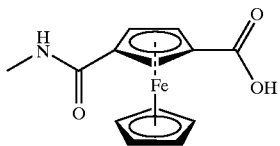

(X1)

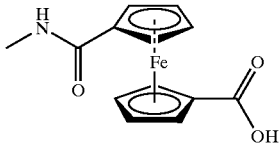

(X2)

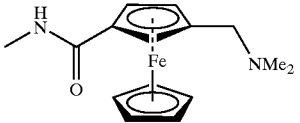

(X3)

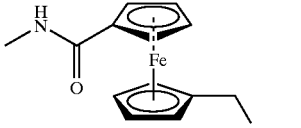

(X4)

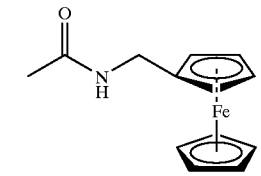

(X5)

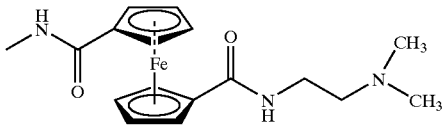

(X6)

The thread intercalator having an electroconductive group comprises not only the oxidative-reductive active moiety and the intercalator moiety but also a linker moiety placed between these moieties. The 1,4-dipropyl-piperazinyl group of the formula is an example of the linker moiety. The piperazinyl group can be replaced with an quaternary imino group. An intercalator of the below-illustrated formula which has a quaternary imino group always is cationic regardless of pH condition. This means that the intercalator is firmly fixed to the DNA hybrid and PNA hybrid. Accordingly, it is favorably employed in the invention. Particularly, the intercalator having a quaternary imino group is preferred in the use in combination with the PNA chip. The linker can be an N-alkyl group having 1 to 6 carbon atoms (e.g, methyl, ethyl, or n-propyl). The oxidative-reductive potential of the ferrocene moiety of the intercalator varies depending upon the nature of the linker moiety.

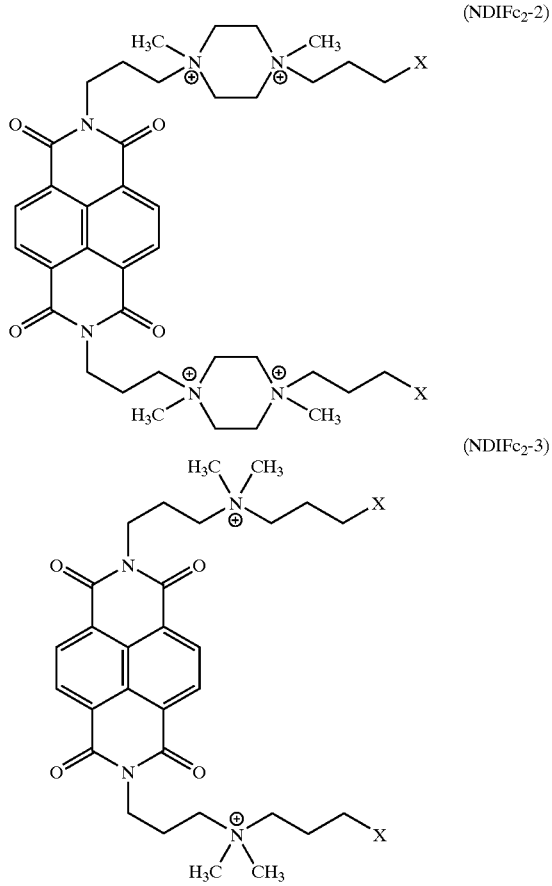

High Sensitive Quantitative Analysis of Sample Nucleic Acid Fragment

FIGS. 1-(1), -(2), -(3), and -(4) schematically illustrate the mechanism of the high sensitive quantitative analysis of sample nucleic acid fragment according to the invention. As described hereinbefore, FIG. 1-(2) illustrates a DNA chip (or PNA chip) 51 of the invention having the spacer molecules 41b on an electroconductive substrate 11 between the fragments 21. The spacer group 41b has a hydrophilic group (e.g., hydroxyl group) 42 on one end which is opposite to the other end at which the spacer is fixed to the substrate When an aqueous solution containing a sample nucleic acid fragment 61 which is complementary to the DNA fragment 21 of the DNA chip 51 is spotted onto the DNA chip, the sample nucleic acid fragment 61 hybridizes with the DNA fragment 21 to give a hybrid double stranded structure 71, as illustrated in FIG. 1-(3). If the hybridization is performed in the presence of an electrochemically active thread intercalator 81a, it enters within the hybrid structure 71 to give an electroconductive portion 81b, as illustrated in FIG. 1-(4). The procedures are generally performed in an aqueous medium. Under this condition, an electric potential is applied to the electroconductive substrate 11, whereby an electric current flows from or to the electroconductive substrate 11 along the hybrid structure 71 having the electroconductive portions 81b. The electric current is then measured The quantitative analysis of the invention is further described below in more detail.

In the first step, an aqueous solution of a sample nucleic acid fragment is prepared. The sample nucleic acid fragment is dissolved or dispersed in an aqueous medium. The aqueous solution of sample nucleic acid fragment is then brought into contact with the DNA chip. The contact can be performed by spotting the aqueous solution on the DNA chip or by immersing the DNA chip in the aqueous solution. The former spotting procedure is preferred. The sample nucleic acid fragment is preferably contained in the spotted aqueous solution in a molar amount of approximately 1 to $10^4$ per one mole of the DNA fragment fixed onto the carrier.

In the DNA chip of the invention, the DNA fragments are fixed onto the solid carrier preferably in an amount of $10^{-20}$ to $10^{-12}$ mol./mm$^2$. In the preferred range, the spacer molecules are well fixed on the solid carrier at free spaces between the fixed DNA fragments, whereby the DNA fragments are well aligned vertically on the carrier and the free spaces are covered with the spacer molecules having a hydrophilic group on the top. The hydrophilic groups on the free spaces are also effective to keep the sample nucleic acid fragment and the thread intercalator from their non-specific adsorption on the solid carrier.

According to the experimental study made by the present inventors, the masked DNA chip (namely, the DNA chip having the spacer molecules fixed between the DNA fragments fixed on a solid carrier) of the invention can be employed for extremely high sensitive quantitative determination of a sample nucleic acid fragment such as a molar amount of $10^{-20}$ to $10^{-16}$ mol., preferably $10^{-20}$ to $10^{-18}$ mole., per 1 mm$^2$ of the solid carrier. If a smaller solid carrier such as an extremely small electroconductive substrate is employed, increased high sensitive quantitative determination of a sample nucleic acid fragment such as a molar amount of up to $10^{-21}$ mole., per 1 mm$^2$ of the carrier may be accomplished.

The DNA chip having on its surface the spotted aqueous solution of a sample nucleic acid fragment is then allowed for stand for a certain period for performing incubation. In the incubation procedure, the thread intercalator is apt to be adsorbed non-specifically by free DNA fragments of the DNA chip which have not participated in the hybridization with the sample nucleic acid fragment. Such unfavorable non-specific adsorption of the intercalator by the free DNA fragments can be obviated by adjusting a salt concentration of the aqueous solution of the sample nucleic acid fragment 0.1 M or more, preferably 0.1 to 1.0 M.

It is not advantageous that the DNA chip having been subjected to hybridization is washed to remove free thread intercalators This is because that, in the washing procedure, the thread intercalators fixed to the hybrid structure may be liberated.

The fixation of the electrochemically active thread intercalator to the hybrid structure can be analyzed by measuring an electric current flowing from or to the solid carrier (i.e., electroconductive substrate) along the hybrid structure having the electrochemically active thread intercalator. The measurement of electric current can be performed by any of known methods such as cyclic voltamography (CV), differential pulse voltamography (DPD), and potentiostat. The differential pulse voltamography is most preferred.

The present invention is further described by the following examples.

EXAMPLE 1

(1) Preparation of DNA Chip

A gold electrode (surface area: 1 mm$^2$) was immersed in an aqueous 2N sodium hydroxide solution for one hour, washed with water, and immersed in conc. nitric acid. The nitric acid was stirred for 15 min. The gold electrode was then washed with super pure water and dried. On thus treated gold electrode was spotted 1 μL of an aqueous solution containing 20 mers of adenine having a mercaptohexyl group at its 5'-terminal (HS-dA$_{20}$, in an amount of $10^{-14}$ mol./μL), and the electrode was allowed to stand for 2 hours. The electrode was washed with super pure water to give a DNA chip The preparation of HS-dA$_{20}$ was made in the manner described in Japanese Patent Provisional Publication No 9-288080.

(2) Fixation of Spacer Molecules

Onto the DNA chip prepared in (1) above was spotted 1 μL of an aqueous 2-mercaptoethanol solution (1 mM). The spotted solution was covered and allowed to stand for 2 hours. The DNA chip was then washed with super pure water, to give the DNA chip of the invention having spacer molecules on its electrode.

(3) Synthesis of Ferrocene-containing Thread Intercalator

The below-illustrated ferrocene-containing naphthalene diimide was synthesized in the manner described in Japanese Patent Provisional Publication No. 9-288080:

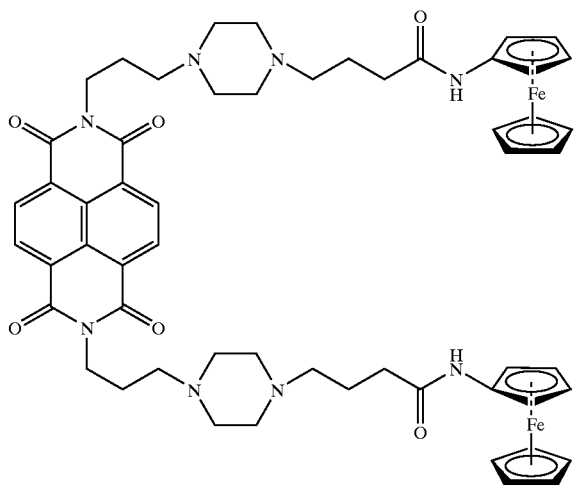

(4) Detection of Sample Nucleic Acid Fragment

A sample nucleic acid fragment, namely, 20 mers of thymine (dT$_{20}$, which was complementary to dA$_{20}$ fixed on the DNA chip) was prepared in a manner similar to that described in the above-mentioned publication.

Onto the DNA chip prepared in (2) above was spotted 1 μL of an aqueous solution of dT$_{20}$, and the DNA chip was allowed to, stand at 25° C. for 30 min., for incubation.

An aqueous electrolytic solution [mixture of aqueous 0.1 M acetic acid/potassium acetate solution (pH 5.6) and aqueous 0.1 M potassium chloride solution) containing 50 μm of the ferrocene-containing naphthalene diimide (prepared in (3) above)] was placed in a thermostat cell maintained at 20° C. In the aqueous electrolytic solution were placed trielectrodes composed of the DNA chip (working electrode), a platinum electrode (opposite electrode), and a silver/silver chloride referential electrode), and differential pulse voltamography (DPV) was performed. Subsequently, a peak current at 460 mV was determined from DPV data.

The above-mentioned detection procedures were repeated using aqueous sample nucleic acid fragment solutions of $10^{-19}$ mol./μL and $10^{-18}$ mol./μL, to determine peak currents at 460 mV from the obtained DPV data.

Figure 2:
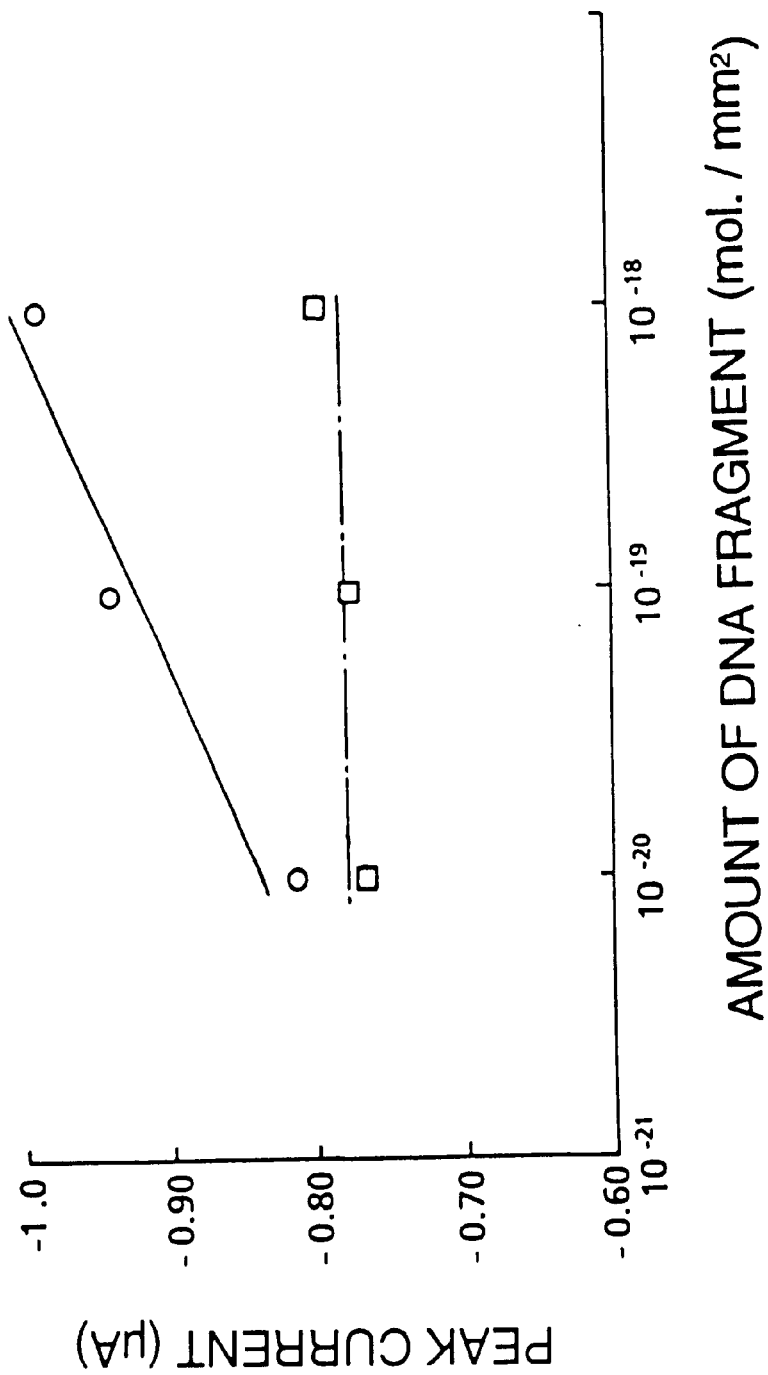
FIG. 2 is a graph indicating an electric current observed in the detection method of the invention as well as an electric current observed in the case that no hybridization occurs between the prove DNA and a target nucleic acid fragment.

The peak currents are graphically illustrated in FIG. 2 by the line connecting the circles.

The above-mentioned detection procedures were repeated for comparison, using an aqueous sample nucleic acid fragment solution containing non-complementary dA$_{20}$ fragment. The peak currents are graphically illustrated in FIG. 2 by the line connecting the blank squares.

FIG. 2 indicates that a linear relationships between the amount of the spotted sample nucleic acid fragment and the peak current is observed in the $10^{-20}$ to $10^{-18}$ mol. range in the use of the DNA chip of the invention. This means that an aqueous sample nucleic acid fragment solution is quantitatively analyzed at least in the range of $10^{-20}$ to $10^{-18}$ mol. per 1 mm$^2$ of the electrode surface.

EXAMPLE 2

(1) Preparation of PNA Chip

On a gold electrode (surface area: 2.25 mm$^2$) having a mercapto group was spotted a phosphate buffer solution containing 1,2-bis(vinylsulfonylacetamide)ethane, to form a free vinylsulfonyl group on the electrode surface. On that surface was further spotted 1 nL of an aqueous solution of the below-illustrated PNA-thymine fragment (PNA-T$_{10}$, 50 nM solution). The spotted solution was allowed to stand for one hour at room temperature. The electrode was then washed with distilled pure water to remove a free PNA-T$_{10}$, whereby give a PNA chip. The preparation of PNA-T$_{10}$ was made in the manner described in P. E. Nielsen et al., Journal of Americal Chemical Society, 114, 1895–1897(1992), ibid., 114, 9677–9678(1992).

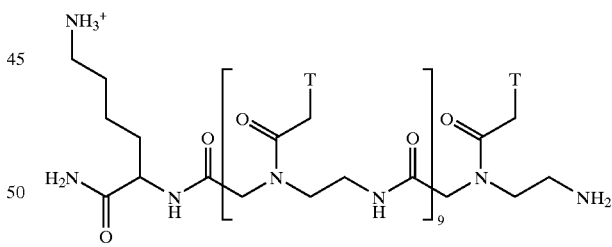

(2) Fixation of Spacer Molecules

Onto the PNA chip prepared in (1) above was spotted 1 μL of an aqueous 2-mercaptoethanol solution (1 mM). The spotted solution was covered and allowed to stand for 2 hours. The PNA chip was then washed with super pure water, to give the PNA chip of the invention having spacer molecules on its electrode.

(3) Detection of Sample Nucleic Acid Fragment

The detection procedures of Example 1-(4) were repeated except for replacing the DNA chip with the PNA chip produced in (2) above.

Almost the same detection results as those observed in Example 1-(4) were obtained.

What is claimed is:

1. A DNA chip comprising a solid carrier and a plurality of DNA fragments having one end fixed onto the solid carrier, wherein a plurality of short chain spacer molecules selected from the group consisting of 2-mercaptoethanol, 3-mercaptopropanol and N,N'-di(3-hydroxy-n-propyl) limidazole-2-thione are fixed through a sulfur atom of the molecule onto a surface area of the solid carrier having no DNA fragments thereon.

2. The DNA chip of claim 1, wherein the solid carrier is an electro-conductive substrate.

3. The DNA chip of claim 1, wherein the DNA fragments are fixed onto the solid carrier in an amount of $10^{-20}$ to $10^{-12}$ moles/mm$^2$.

4. A process for preparing a DNA chip comprising a solid carrier and a plurality of DNA fragments fixed onto the solid carrier at each one end, wherein a plurality of short chain spacer molecules having a hydrophilic moiety at each one end are fixed through an opposite end thereof onto a surface area of the solid carrier having no DNA fragments thereon which comprises the steps of applying onto a solid carrier an aqueous solution of a plurality of DNA fragments dissolved or dispersed in an aqueous medium to fix the DNA fragments onto the solid carrier, and applying onto a surface area of the solid carrier having no DNA fragments thereon an aqueous solution of short chain spacer molecules each having at one end a hydrophilic moiety and at an opposite end thereof a moiety reactive to fix to the solid carrier.

5. The process of claim 4, wherein the short chain spacer molecules are elected from the group consisting of 2-mercaptoethanol 3-mercaptopropanol, and N,N'-di(3-hydroxy-n-propyl)imidazole-2-thione.

* * * * *